United States Patent [19]

Nimry et al.

[11] 4,391,967

[45] Jul. 5, 1983

[54] POLYIMIDES-POLYAMIDES FROM TRICYCLO [4.2.1.0$^{2,5}$] NONANE-3,4-DIMETHYL-3,4,7,8-TETRACARBOXYLIC ACID DIANHYDRIDE AND DICARBOXYLIC ACIDS

[75] Inventors: Tayseer S. Nimry, Wheaton; Ellis K. Fields, River Forest, both of Ill.

[73] Assignee: Standard Oil Company (Indiana), Chicago, Ill.

[21] Appl. No.: 427,017

[22] Filed: Sep. 29, 1982

Related U.S. Application Data

[63] Continuation-in-part of Ser. No. 254,347, Aug. 19, 1981, Pat. No. 4,358,582.

[51] Int. Cl.$^3$ .............................................. C08G 73/14
[52] U.S. Cl. ..................... 528/189; 428/458; 428/473.5; 428/474.4; 528/125; 528/128; 528/188; 528/206; 528/208; 528/220; 528/229; 528/352; 528/353
[58] Field of Search .................. 428/458, 473.5, 474.4; 528/125, 128, 188, 189, 206, 208, 220, 229, 352, 353; 549/234

[56] References Cited

U.S. PATENT DOCUMENTS

| | | | |
|---|---|---|---|
| 3,257,418 | 6/1966 | Vermont | 549/234 |
| 3,299,102 | 1/1967 | Bradshaw | 549/234 |
| 3,413,316 | 11/1968 | Bradshaw | 549/234 |
| 3,423,431 | 1/1969 | Starr et al. | 549/234 |
| 3,472,749 | 10/1969 | Bradshaw | 549/234 |
| 3,503,998 | 3/1970 | Schuller et al. | 549/234 |
| 4,358,580 | 11/1982 | Nimry | 528/188 |
| 4,360,657 | 11/1982 | Nimry et al. | 528/188 |

*Primary Examiner*—Lester L. Lee
*Attorney, Agent, or Firm*—Gunar J. Blumberg; William T. McClain; William H. Magidson

[57] ABSTRACT

This invention relates to novel polyimides-polyamides and copolyimides-polyamides prepared from the novel nonaromatic dianhydrides or mixtures of these with other dianhydrides. Tricyclo [4.2.1.0$^{2,5}$] nonane-3,4-dimethyl-3,4,7,8-tetracarboxylic acid dianhydride (I). I is used to prepare novel polyimides-polyamides which are useful in preparing molded articles, fibers, laminates and coatings.

8 Claims, No Drawings

POLYIMIDES-POLYAMIDES FROM TRICYCLO [4.2.1.0$^{2,5}$] NONANE-3,4-DIMETHYL-3,4,7,8-TETRACARBOXYLIC ACID DIANHYDRIDE AND DICARBOXYLIC ACIDS

This application is a C.I.P. of Ser. No. 254,347 filed Aug. 19, 1981 and now U.S. Pat. No. 4,358,582.

BACKGROUND OF THE INVENTION

1. Field of the Invention

The field of this invention relates to novel polyimides-polyamides and copolyimides-polyamides prepared from the novel nonaromatic dianhydrides or mixtures of these with other dianhydrides. Tricyclo [4.2.1.0$^{2,5}$] nonane-3,4-dimethyl-3,4,7,8-tetracarboxylic acid dianhydride (I). I is used to prepare novel polyimides-polyamides which are useful in preparing molded articles, fibers, laminates and coatings.

2. Background

British Patent Specification No. 570,858 discloses various processes for making fiber forming polymers. The prior art does not disclose or contemplate I the polyimides-polyamides prepared from I which are useful as moldings, fibers, laminates and coatings.

The general object of this invention is to provide novel polyimides-polyamides and copolyimides-polyamides based on the new dianhydride I, dicarboxylic acids, and one or more diamine moieties. A more specific object of this invention is to provide polyimides-polyamides from I, dicarboxylic acids and aliphatic, cycloaliphatic, araliphatic and aromatic diamine moieties. It is also suitable to use a mixture of I and another aromatic or aliphatic dianhydrides with one or more dicarboxylic acids to manufacture copolyimides-copolyamides.

We have found that novel polyimides-polyamides can be formed by reacting I and dicarboxylic acids with diamines. I reacts readily with the diamine and dicarboxylic acids to form high molecular weight polyimide-polyamides. In the novel process both aliphatic and aromatic diamines can be polymerized with I and a dicarboxylic acid or derivative in the melt to form high molecular weight polyimides-polyamides and copolyimides-copolyamides.

Our process for the manufacture of the novel polyimides-polyamides and copolyimides-copolyamides comprises reacting about equal molar amounts of I and a dicarboxylic acid with a primary diamine or a mixture of primary diamines. The molecular ratio of I together with a dicarboxylic acid to the primary diamine may be in the range of 1.2 to 1 preferably in the range of 1 to 1. Suitably, the reaction is conducted as a batch reaction at a temperature of about 130° to 300° C. for a period of about 2 to 8 hours in a nitrogen-containing organic polar solvent such as N-methyl-2-pyrrolidinone, N,N-dimethylacetamide or pyridine. I can be replaced partially by another dianhydride either aromatic or aliphatic or by a dicarboxylic acid, mixtures of dicarboxylic acids or their derivatives.

The other dianhydrides are characterized by the following formula:

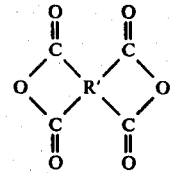

wherein R' is a tetravalent organic radical selected from the group consisting of aromatic, aliphatic, cycloaliphatic, heterocyclic, combination of aromatic and aliphatic, and substituted groups thereof. However, the preferred dianhydrides are those in which the R' groups have at least 6 carbon atoms, wherein the 4 carbonyl groups of the dianhydride are each attached to separate carbon atoms and wherein each pair of carbonyl groups is directly attached to adjacent carbon atoms in the R' group to provide a 5-membered ring as follows:

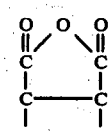

The preferred dianhydrides, as recited above, yield upon reaction with the diamines polyimide structures having outstanding physical properties. Illustrations of dianhydrides suitable for use in the present invention include: pyromellitic dianhydride; 2,3,6,7-naphthalene tetracarboxylic dianhydride; 3,3',4,4'-diphenyl tetracarboxylic dianhydride; 1,2,5,6-naphthalene tetracarboxylic dianhydride; 1,2,3,4-cyclopentane tetracarboxylic dianhydride; 2,2',3,3'-diphenyl tetracarboxylic dianhydride; 2,2-bis(3,4-dicarboxyphenyl) propane dianhydride; 2,3,4,5-pyrrolidine tetracarboxylic dianhydride; 3,4,9,10-perylene tetracarboxylic dianhydride; bis(3,4-dicarboxyphenyl) ether dianhydride; ethylene tetracarboxylic dianhydride; 3,3', 4,4'-benzophenonetetracarboxylic dianhydride; bis(3,4-dicarboxyphenyl)sulfide dianhydride; bis(3,4-dicarboxyphenyl)sulfone dianhydride; bis(3,4-dicarboxyphenyl)methane dianhydride; 1,4,5,8-naphthalenetetracarboxylic dianhydride; tricyclo [4,2,2,0$^{2,5}$] dec-7-ene-3,4,9,10-tetracarboxylic dianhydride; 3,6-ethenohexahydropyromellitic dianhydride; cyclobutane-1,2,3,4-tetracarboxylic dianhydride; and 1,3-dimethylcyclobutane-1,2,3,4-tetracarboxylic dianhydride. The polycondensation can also be carried out as a continuous process. The polycondensation can suitably be carried out at a temperature of 130° C. to 300° C., preferably at a temperature of 180° to 250° C. The novel polyimides-polyamides of this invention have the following recurring structure wherein R is a divalent aliphatic or aromatic hydrocarbon radical.

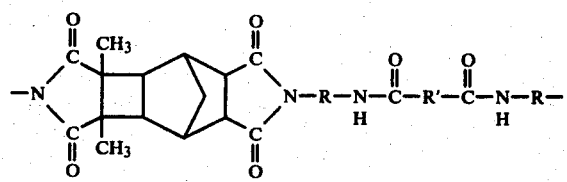

The radical R and R' can be aliphatic or aromatic divalent hydrocarbons. Suitably the radicals are divalent aliphatic hydrocarbons of 2 to 18 carbon atoms or aromatic hydrocarbons from 6 to 20 carbon atoms. R is advantageously an aromatic hydrocarbon radical containing from 6 to 10 carbon atoms joined directly or by stable linkage comprising —O—, methylene,

—SO—, —SO$_2$—, and —S— radicals.

The radical R is derived from aliphatic, araliphatic or cycloaliphatic diamines such as ethylenediamine, propylenediamine, 2,2-dimethylpropylene diamine, tetramethylene diamine, hexamethylene diamine, octamethylene diamine, nonamethylene diamine, decamethylene diamine, dodecamethylene diamine, 4,4'-diaminodicyclohexylethane, xylylene diamine and bis (aminomethyl) cyclohexane. Suitable aromatic diamines useful in our process include para- and meta-phenylenediamine, 4,4'-oxydianiline, thiobis (aniline), sulfonylbis (aniline), diaminobenzophenone, methylenebis (aniline), benzidine, 1,5-diaminonaphthalene, oxybis (2-methylaniline), thiobis (2-methylaniline), and the like. Examples of other useful aromatic primary diamines are set out in U.S. Pat. Nos. 3,494,890 (1970) and 4,016,140 (1972) both incorporated herein by reference. The preferred diamines are hexamethylene diamine and dodecamethylene diamine.

The dicarboxylic acids suitable for our process comprise the following structure.

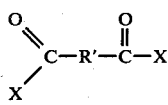

where X is OH, Cl, or O alkyl wherein the alkyl group comprises about 1 to about 5 carbon atoms and R' is a divalent aromatic or aliphatic radical. Advantageously R' is a divalent aliphatic hydrocarbon containing about 2–18 carbon atoms or an aromatic divalent hydrocarbon radical comprising about 1–3 benzene rings or R' is a heterocyclic organic compound. The dicarboxylic acids suitable for use in our process include such acids or their halides or esters as oxalic, glutaric, adipic, azelaic, terephthalic, isophthalic, biphenyl-4'-dicarboxylic, 2,6-naphthalene dicarboxylic, and pyridine-2,4- and 3,5-dicarboxylic.

In some cases the polyimide-polyamide may be further polymerized under "solid state polymerization" conditions. The term solid state polymerization refers to chain extensions of polymer particles under conditions where the polymer particles retain their solid form and do not become a fluid mass. The solid state polymerization can be carried out below the melting point of the polyimide-polyamide and can be conducted in several ways. However, all techniques require heating the ground or pelletized polyimide-polyamide below the melting point of the polyimide-polyamide, generally at a temperature of about 175° to 300° C. while either sparging with an inert gas such as nitrogen or operating under vacuum. In cases where the polyimides-polyamides and copolyimides-polyamides have a low melt temperature, they can be polymerized in the melt under vacuum in thin sections or using thin film reactors known in the art.

Injection molding of the novel polyimide-polyamide is accompanied by injecting the polyimide-polyamide into a mold maintained at a temperature of about 25° C. to 150° C. In this process a 20 second to 1 minute cycle is used with a barrel temperature of about 125° C. to 350° C. The latter will vary depending on the $T_g$ of the polymer being molded. The injection molding conditions are given in Table 1.

TABLE 1

| Mold Temperature | 25° to 150° C. |
|---|---|
| Injection Pressure | 15,000 to 19,000 psi and held for 1 to 3 seconds |
| Back Pressure | 100 to 220 psi |
| Cycle Time | 25 to 28 seconds |
| Extruder: | |
| Nozzle Temperature | 125° C. to 350° C. |
| Barrels: | |
| Front heated to | 125° C. to 350° C. |
| Screw: | |
| 20 to 25 revolutions/minute | |

The novel polyimides-polyamides having excellent mechanical and thermal properties and can readily be molded into useful articles or formed into fibers, films, laminates or coatings.

Infrared spectra of the polyimides-polyamides have confirmed the polyimide-polyamide structures.

Analysis of the polyimides-polyamides by thermal gravimetric analysis shows excellent stability. Glass transition temperature Tg of the polyimides-polyamides varied with the particular diamine used. Values range from a Tg of 65° C. to 115° C.

Diamines with the amino groups attached directly to the aromatic ring are suitably polymerized with I by solution condensation in organic polar solvents. The include N,N-dimethylacetamide, N-methyl-2-pyrrolidinone, N,N-dimethylformamide, pyridine, and the like.

The following examples illustrate the preferred embodiment of the invention. It will be understood that the examples are for illustrative purposes only and do not purport to be wholly definitive with respect to conditions or scope of the invention.

EXAMPLE 1

Synthesis of Tricyclo [4.2.1.02,5] Nonane-3,4-Dimethyl-3,4,7,8-Tetracarboxylic Acid Dianhydride (I)

I of the following structure:

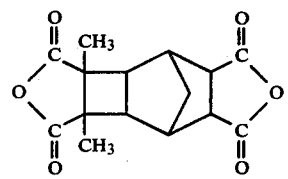

is prepared by a photocycloaddition reaction between dimethylmaleic anhydride (II) and 5-norbornene-2,3-dicarboxylic anhydride (III). To a 500-ml pyrex erlenmeyer flask equipped with a condenser was added 5.0 g (40 mmole) of II, 6.51 g (40 mmole) of III and 0.3 g of benzophenone. The mixture was dissolved in 100 ml toluene and exposed to light from a GE sunlamp for 64 hours. During this time the insoluble photodimer of II was filtered off at several intervals. At the end of the irradiation the filtrate was concentrated to approximately 50 ml. on a rotary evaporator. I precipitated and was collected and washed with a small volume of cold toluene. Approximately one-half of II dimerized to the useful tetramethylcyclobutane tetracarboxylic dianhydride.

The yield of I based on the remaining dimethylmaleic anhydride was 30%. Its melting point after recrystallization from acetone is 315°-8° C. (dec.) Anal. Calcd. for $C_{15}H_{14}O_6$: C,62.07, H,4.83. Found: C,62.35; H, 4.95.

The mass spectrum recorded at a probe temperature of approximately 220° C. is consistent with the proposed configuration for I. A partial list of the ions detected is shown here:

|  | Mass | Ion Identification | Fragmentation |
|---|---|---|---|
|  | 290 | $C_{15}H_{14}O_6$ | $I^+$, molecular ion |
|  | 275 | $C_{14}H_{11}O_6$ | I—CH$_3$ |
|  | 272 | $C_{15}H_{12}O_5$ | I—H$_2$O |
|  | 262 | $C_{14}H_{14}O_5$ | I—CO |
|  | 245 | $C_{14}H_{13}O_4$ | I—COOH |
|  | 244 | $C_{14}H_{12}O_4$ | I—CO—H$_2$O |
|  | 234 | $C_{13}H_{14}O_4$ | I-CO—CO |
| (base peak) | 218 | $C_{13}H_{14}O_3$ | I—CO—CO$_2$ |

To a stirred solution of 2.9 g (0.01 mole) of Compound I and 1.94 g (0.01 mole) of dimethyl terephthalate in 45 ml of N-methyl-2-pyrrolidinone (NMP) at 80° C. under N$_2$ at 50 cc/min. was added a solution of 4.0 g-(0.02 mole) of 1,12-dodecanediamine in 10 ml. NMP in one portion. Temperature was increased to 175° C. and kept there for 1 hour, then, by distilling the NMP, increased to 220° C. for 1 hour. The solution was cooled to 90° C. and added to 400 ml. of water in a blender. The precipitated polyimide-polyamide was collected on a filler funnel, washed with 4 100 ml. portions of water, and dried in a vacuum oven at 90° C. for 6 hours. The polyimide-polyamide weighed 7.29 g (93% yield) and had an intrinsic viscosity in 60/40 phenol/terachloroethane of 0.89.

Analysis. Calcd. for $(C_{47}H_{68}N_4O_6)$: C, 71.9; H, 8.7; N, 7.1. Found: C, 71.2; H, 8.4; N, 6.9.

EXAMPLE 3

To a stirred mixture of 2.9 g (0.01 mole) of Compound I and 1.94 g (0.01 mole) of dimethyl isophthalate in 50 ml. NMP at 80° C. under N$_2$ at 50 cc/min. was added a solution of 1.2 g (0.02 mole) of 1,6-hexanediamine in 10 ml. NMP. The heating regime and workup were as in Example 2, giving a white polyimide-polyamide, 4.49 g (89% yield) with an intrinsic viscosity of 0.46.

Analysis. Calcd. for $(C_{35}H_{44}N_4O_6)_n$: C, 68.2; H, 7.1; N, 9.1. Found: C, 67.7; H, 7.3; N, 8.8.

EXAMPLE 4

To a stirred solution of 2.9 g of Compound I and 1.46 g (0.01 mole) of adipic acid in 40 ml. NMP at 85° C. under N$_2$ at 50 cc/min. was added a solution of 4.0 g (0.02 mole) oxybisaniline in 15 ml. NMP. Heating and workup as in Example 2 gave 6.88 g (90% yield) of off-white polyimide-polyamide that had an intrinsic viscosity of 0.41.

Analysis. Calcd. for $(C_{45}H_{30}N_4O_8)_n$: C, 71.6; H, 4.0; N, 7.4 Found: C, 70.7; H, 4.1; N, 7.2.

We claim:
1. A polyimide-polyamide comprising the following recurring structure:

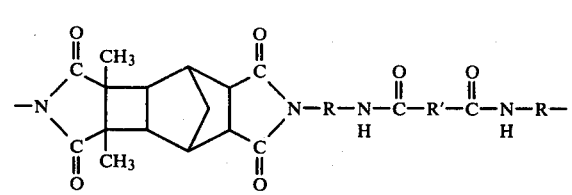

wherein R' is the same or different divalent aliphatic, cycloaliphatic, araliphatic or aromatic hydrocarbon radicals the term "R has the same meaning as R' or is an aromatic hydrocarbon having from about 6 to about 10 carbon atoms joined directly or by a stable linkage selected from the group consisting of —O—, methylene,

—SO—, —SO$_2$— or —S— radicals".

2. The polyimide-amide of claim 1 wherein R and R' are divalent aliphatic hydrocarbons from about 2 to about 18 carbon atoms.

3. The polyimide-amide of claim 1 wherein R and R' are divalent aromatic hydrocarbons from 6 to 20 carbon atoms.

4. The polyimide-polyamide of claim 1 wherein R comprises from about 6 to about 10 carbon atoms joined directly or by stable linkage selected from the group consisting of —O—, methylene,

—SO—, —SO$_2$— or —S— radicals.

5. The polyimide-amide of claim 1 wherein the polyimide-amide is in the form of a molded object.

6. The polyimide-amide of claim 1 wherein the polyimide-amide is in the form of a fiber.

7. The polyimide of claim 1 wherein the polyimide is in the form of a film.

8. The polyimide of claim 1 wherein the polyimide is in the form of a metal coating suitable for electrical service.

* * * * *

UNITED STATES PATENT AND TRADEMARK OFFICE
CERTIFICATE OF CORRECTION

PATENT NO. : 4,391,967

DATED : July 5, 1983

INVENTOR(S) : Tayseer S. Nimry et al.

It is certified that error appears in the above-identified patent and that said Letters Patent is hereby corrected as shown below:

| Column | Line | |
|---|---|---|
| 3 | 1 | "R is" should read --R'-- |
| 3 | 18 | "para- and meta-" should read --para- and meta--- |
| 4 | 55 | "O   O" should read --O   I   O-- |
| 4 | 43 | "[4.2.1.02,5]" should read --[4.2.1.2,5]-- |
| 5 | 22 | "   " should read --Example 2-- |
| 6 | 21 | " "R " should read --R-- |
| 6 | 30 | "radicals" " should read --radicals-- |

Signed and Sealed this

Twenty-first Day of February 1984

[SEAL]

Attest:

GERALD J. MOSSINGHOFF

Attesting Officer    Commissioner of Patents and Trademarks